US009714935B2

(12) United States Patent
Mun et al.

(10) Patent No.: US 9,714,935 B2
(45) Date of Patent: Jul. 25, 2017

(54) NON-INVASIVE METHOD FOR MEASURING PROLIFERATION AND DIFFERENTIATION STATE OF CELLS BY USING MAGNETIC RESONANCE SPECTROSCOPY, AND CELL PROLIFERATION AND DIFFERENTIATION MARKER FOR MAGNETIC SPECTROSCOPY USED THEREFOR

(71) Applicant: INJE UNIVERSITY INDUSTRY-ACADEMIC COOPERATION FOUNDATION, Gyeongsangnam-do (KR)

(72) Inventors: Chi Woong Mun, Busan (KR); Moo Young Jang, Chungcheongbuk-do (KR); Song I Chun, Busan (KR); Bok Man Kang, Gyeongsangnam-do (KR); So Young Kwak, Gyeongsangnam-do (KR)

(73) Assignee: INJE UNIVERSITY INDUSTRY-ACADEMIC COOPERATION FOUNDATION, Gyeongsangnam-do (KR)

( * ) Notice: Subject to any disclaimer, the term of this patent is extended or adjusted under 35 U.S.C. 154(b) by 0 days.

(21) Appl. No.: 14/378,092

(22) PCT Filed: Jul. 29, 2013

(86) PCT No.: PCT/KR2013/006755

§ 371 (c)(1),
(2) Date: Dec. 23, 2014

(87) PCT Pub. No.: WO2014/021592

PCT Pub. Date: Feb. 6, 2014

(65) Prior Publication Data

US 2015/0153324 A1 Jun. 4, 2015

(30) Foreign Application Priority Data

Jul. 30, 2012 (KR) ........................ 10-2012-0083135

(51) Int. Cl.

| | |
|---|---|
| ***G01N 33/48*** | (2006.01) |
| ***G01N 33/50*** | (2006.01) |
| ***G01N 24/08*** | (2006.01) |
| ***G01R 33/465*** | (2006.01) |
| *G06G 7/58* | (2006.01) |

(52) U.S. Cl.

CPC ......... *G01N 33/5005* (2013.01); *G01N 24/08* (2013.01); *G01R 33/465* (2013.01); *G01N 2405/00* (2013.01); *G01N 2410/00* (2013.01)

(58) Field of Classification Search

CPC ........... G06F 19/18; G06F 19/22; G06F 19/24
See application file for complete search history.

(56) References Cited

FOREIGN PATENT DOCUMENTS

| | | |
|---|---|---|
| JP | 2008-529007 | 7/2008 |
| JP | 2011-510271 | 3/2011 |
| KR | 10-0680699 | 2/2007 |
| WO | 2006081471 | 8/2006 |
| WO | 2009089500 | 7/2009 |

OTHER PUBLICATIONS

Mun, Chi Ung. Nondestructive measurement of metabolite from stem cell differentiation using MRI and MRS.: Final Report of Junior Researcher Support Business. Jun. 2012.
Lee, Chae Heuck et al., "In Vivo Proton MR Spectroscopic Change of Experimental Rat Brain Abscess Model". J Korean Neurosurg Soc. Oct. 1999, vol. 28, pp. 1429-1439.
International Search Report for PCT/KR2013/006755, Aug. 29, 2013.

*Primary Examiner* — Eric S Dejong
(74) *Attorney, Agent, or Firm* — Fulwider Patton LLP

(57) ABSTRACT

Provided are a noninvasive measurement of cell signals and a method thereof, wherein the measurement method can ascertain cell proliferation and differentiation states using MRS and can enable cells to be reused so that cell states can be evaluated with improved reproducibility and reliability. And since the cell signals are noninvasively measured using the MRS, the corresponding cells can be reused so that the cost and time needed for one experiment can be remarkably reduced.

9 Claims, 7 Drawing Sheets

NON-INVASIVE METHOD FOR MEASURING PROLIFERATION AND DIFFERENTIATION STATE OF CELLS BY USING MAGNETIC RESONANCE SPECTROSCOPY, AND CELL PROLIFERATION AND DIFFERENTIATION MARKER FOR MAGNETIC SPECTROSCOPY USED THEREFOR

CROSS-REFERENCE TO RELATED APPLICATIONS

This application is the U.S. national stage application of International Patent Application No. PCT/KR2013/006755, filed Jul. 29, 2013, which claims priority to Korean Application No. 10-2012-0083135, filed Jul. 30, 2012, the disclosures of each of which are incorporated herein by reference in their entirety.

TECHNICAL FIELD

The present invention relates to repetitive noninvasive measurement of cell signals for living cells which maintain vital activity, and a method thereof.

BACKGROUND ART

Cell culture is a complex process by which cells in the most basic unit of human body are continuously grown under controlled conditions, generally outside of their natural environment, or the cells are developed into other cells having different properties by adding a specific growth factor thereto. In terms of modern science, a cell culture technology has been placed in the field of basic essentials, and in particular, in the field of medical engineering, the cell culture technology has been widely used in judging whether or not a license for a drug is approved through cytotoxicity assessment using a preclinical test and has been also applied to researches for finding the mechanism of diseases.

As cells show different shapes and characteristics depending on derived species or the parts of tissues, the cells have different types of metabolites generated through metabolism. In particular, in the case of stem cells which can be differentiated into various tissue cells, there are specific metabolites depending on differentiated cell types.

In general, most of experiments for ascertaining whether or not cells are differentiated are performed in such a way as to observe a result obtained from reaction to a reagent, and a staining, PCR (Polymerase Chain Reaction) method and the like fall into such a way. Since the described methods are invasive methods in which cells cannot be reused after reaction, in order to verify reproducibility through repeated experiments using cells, a large number of samples are needed for one experiment, and thus, the costs required for one experiment are increased. Also, the existing experimental method should endure an error generated by applying the experiment to different samples, and due to this, it has a limit of the reduction in reproducibility and reliability of experimental results.

A magnetic resonance spectroscopy (hereinafter referred to as 'MRS' or 'NMR') and a magnetic resonance imaging (hereinafter referred to as 'MRI') are techniques capable of noninvasively and nondestructively measuring bio-signals, and in the current medical field, the MRI is drawing attention as a diagnostic equipment thanks to a high soft tissue contrast and various contrast parameters of the MRI. However, the MRI and MRS have low sensitivity in regard to a volume, and thus show low resolution with respect to small objects of less than a certain thickness. In order to overcome this problem, an MR machine of a higher magnetic field is needed, but even the MR machine is difficult to be applied to cells in the unit of μm.

DISCLOSURE OF INVENTION

Technical Problem

An aspect of the present invention provides a measurement method of cell states that noninvasively measures the signals of living cells being in vital activity using MRS which is noninvasive equipment and thus enables the corresponding cells to be reused so that the cost and time needed for one experiment can be reduced.

Moreover, another aspect of the present invention provides a biomarker capable of evaluating proliferation and differentiation information on respective cells through quantitative analysis for peaks shown in MRS.

A definitive aspect of the present invention provides a measurement method that noninvasively measures cell signals using MRS which is a noninvasive equipment and thus enables the corresponding cells to be reused so that the cost and time needed for one experiment can be remarkably reduced, and reliability and reproducibility of research results can be increased through repetitive experiments for same samples.

Solution to Problem

In order to realize the above measurement method, the present invention may provide a novel cell differentiation biomarker for respective cells through quantitative analysis of peaks shown in MRS in consideration of the fact that the type and amount of metabolites shown depending on cell types are fixed. Thus, cell signals are noninvasively measured using the MRS which is a noninvasive equipment so that a measurement method which enables the corresponding cells to be reused can be provided, thereby remarkably reducing the cost and time needed for one experiment.

In particular, the present invention may provide a measurement method of cell states using MRS, which is to analyze MRS data obtained from cell samples having a constant concentration and produce cell proliferation and differentiation information by measuring the spectrum signals of metabolites derived from the cell samples.

In this case, area values of the metabolite peaks may be used as a biomarker for determining chondrogenesis, and the metabolites may be fatty acids, leucine, alanine, phosphocholine, glutamine, GABA and the like, and the differentiation may be evaluated using any one selected from among the metabolites or an entire change aspect thereof.

Also, according to an embodiment of the present invention, the chondrogenesis may be determined using a fatty acid of 1.30 ppm among the aforesaid metabolites, or the fatty acid may be used as a biomarker for determining adipogenesis.

In the measurement method of cell states according to the present invention, it is preferable that a biomarker for cell differentiation measurement be determined by normalizing MRS signals of the cells to the number of used cells in experiment, and analyzing the metabolites measured based on the data of the normalized signals. In this case, the analysis of the metabolites may be performed with the quantitative analysis of integral values of spectral peaks shown by the metabolites generated during a cell differentiation period.

In the measurement method of cell states according to the present invention, in order to overcome low sensitivity of MRS, a concentration of cells seeded in a scaffold providing a basis for 3 dimensional (3D) culture may be in a range of $1\times10^6$~$1\times10^7$/ml or may be in a range beyond the range, and the cell samples may result from mixing a mixture of a medium and cells to a scaffold solution in a ratio of 1 to 1 and solidifying the mixed mixture and scaffold solution. In this case, any one among cell culture scaffolds which have been commercialized, such as alginate, fibrin gel, agarose gel, and PLGA may be used as the scaffold.

Advantageous Effects of Invention

According to the present invention, a biomarker capable of ascertaining proliferation and differentiation information for respective cells can be provided by the quantitative analysis of peaks shown in MRS.

In particular, since cell signals are noninvasively measured using MRS which is noninvasive equipment, a measurement method for enabling corresponding cells to be reused is provided so that the cost and time required for one experiment can be remarkably reduced.

That is, since only samples to be used for one experiment are required, the time can be saved compared to the existing method, the reliability and reproducibility of research results can be increased through a repeated experiment regarding the same samples, and the measurement of the present invention can be performed without a reference material which is necessarily required upon a measurement using MRS. Also, since MR spectra are quantifiable based on a concentration of cells, the loss of cells due to toxicity of the reference material, such the like of TSP, can be prevented, and the problems of a reduction in accuracy of experimental results shown due to an error in an amount of the reference material generated at the time of injecting the reference material and a re-test which should be performed due to the reduction in accuracy can be solved.

THE DESCRIPTION OF REFERENCE NUMERALS OF THE DRAWINGS

Figure 1:
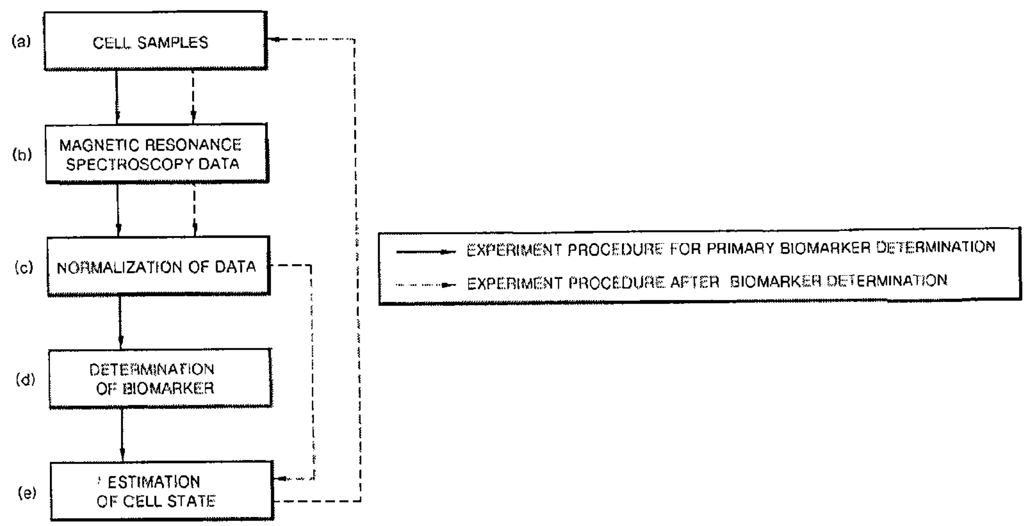
FIG. 1 is a flow chart illustrating a measurement method of cell states using MRS according to the present invention, and a method of applying a proliferation/differentiation marker (biomarker) used therefor.

10: NMR tube
20: Culture scaffold
30: Medium
40: Solid material
50: Radiofrequency (RF) coil for signal measurement
60: Vessel (NMR tube)

Mode for the Invention

Hereinafter, the configurations and operations according to the present invention will be described in detail with reference to the accompanying drawings. In the explanation with reference to the accompanying drawings, regardless of reference numerals of the drawings, the same numerals refer to the same elements through the specification, and repeated explanation thereon is omitted.

The present invention provides a measurement method that can further objectively evaluate cell states by ascertaining cell proliferation and differentiation states using MRS and enabling cells to be reused, and provides a biomarker depending on differentiated cell types using MRS data.

For this, the present invention provides a measurement method of cell states using MRS, which is carried out in such a manner as to analyze MRS data obtained repeatedly at a specific time during inducing differentiation from stem cell samples having a constant concentration, and producing cell proliferation and differentiation information by measuring metabolite signals from the cell samples. That is, based on the fact that the type and amount of metabolites produced depending on cell types are fixed, a novel cell differentiation biomarker for each cell may be provided through quantitative analysis of peaks shown in the MRS.

FIG. 1 is a flow chart illustrating a measurement method of cell states using MRS according to the present invention, and a method of applying a differentiation marker (biomarker) used therefor.

Referring to FIG. 1, the measurement method of cell states according to the present invention may measure MRS signals from basically prepared cells, normalize the MRS signals to a concentration of the cells measured, and enable differentiation and proliferation states of the cells to be decided using a differentiation marker (hereinafter referred to as the 'biomarker') determined through the comparison of metabolites showing changes in spectra measured during differentiation of the cells.

That is, upon analyzing the MRS data obtained during proliferation and differentiation periods, a biomarker which is determined by measuring the integral values of metabolite peaks after normalizing respective spectra to a concentration of cells measured may quantitatively show the proliferation and differentiation states of the cells. Accordingly, even though cell samples are prepared under different situations or conditions, when the types of the cell samples are identical to each other, and a concentration of the cells measured at the time of the preparation and differentiation type of the cells are known, proliferation/differentiation degrees, namely, cell states may be decided and compared by normalizing the spectra of metabolites produced during differentiation to the number of cells and comparing respective integral values.

Following a primary test for determining a biomarker, an additional process for determining a biomarker may be excluded, and cell states may be decided and compared by measuring MRS data again with the cells which have been used.

According to the present invention, cell types to which the noninvasive measurement method of cell proliferation and differentiation states using the MRS can be applied are not limited, and in a case where the cell types are different from each other or the differentiation types are different from each other, if only a concentration of the metabolites found in the corresponding cells is specified, a variety of metabolites may be utilized as a biomarker for evaluating cell proliferation and differentiation states.

Figure 2:
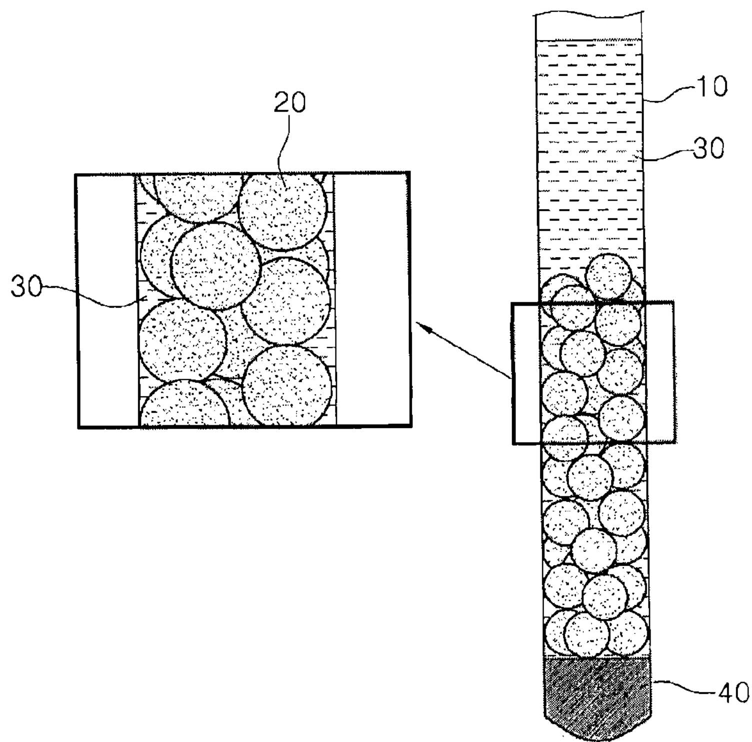
FIG. 2 is a mimetic diagram of an NMR tube in which a medium and a three dimensional (3D) scaffold having cultured cells are put.
Figure 3:
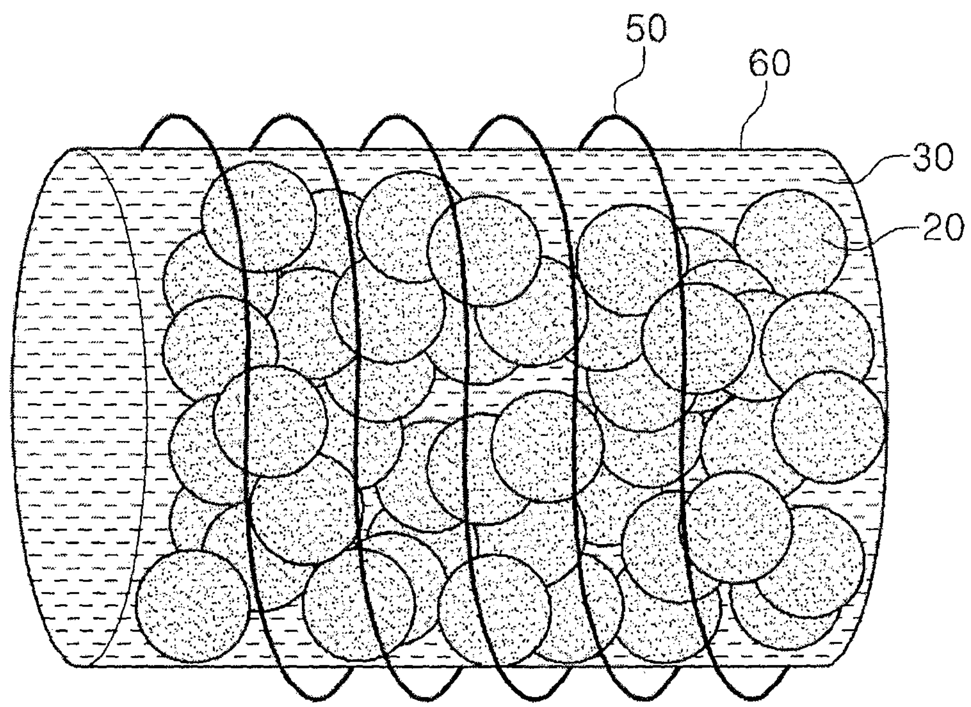
FIG. 3 is a mimetic diagram of a container in which a medium and cells surrounded by a radiofrequency (RF) coil for MR measurement and the 3D scaffold positioned at the inside of the coil are put.

FIGS. 2 and 3 show cell samples used in the noninvasive measurement method of cell proliferation and differentiation states and a principle of the measurement method using MRS according to the present invention. However, the measurement method and principle, which will be hereinafter explained, are only examples, but the present invention should not be limited thereto, and those skilled in the art will appreciate that various modifications, additions and substitutions are possible, without departing from the scope and spirit of the present embodiment. For example, the types of cell samples or the types of differentiations concretely shown in the examples and strength of a magnetic field applied for obtaining MRS data or a concentration of cells may be variously changed. In addition, differences related to the modification and application should be interpreted to be included in the scope of the present invention as defined in the accompanying claims.

FIG. 2 is an entire mimetic diagram of samples which are subject to the present invention. The cell samples are cultured in a 3D culture scaffold (20) which is placed inside an NMR tube (10), and a liquid filled in the periphery of the scaffold (20) is a medium (30) supplying nutrients necessary for the survival of cells. That is, the cell samples according to the present invention maintain viability by receiving nutrients provided from the medium (30), and as a solid material (40), a material such as 'agarose gel' may be filled in a lower part of the NMR tube so that the cell samples can be adjusted to be positioned at the center of the RF coil and thus optimum MR signals can be acquired.

In particular, with regard to the method of culturing cells in the scaffold (20) according to the present invention, in order to overcome the low sensitivity of MRS, a method of 3D culturing cells may be applied to the scaffold having a dimensional structure, and various scaffolds of appropriate materials such as alginate, fibrin gel, and a polymeric material (PLGA) may be selected depending on cell types. A method of seeding cells in a 3D scaffold, and thereafter, enabling the 3D scaffold including the seeded cells to be suspended in the medium for supply of the medium, and a method of using a culture chamber having a turning force to enable the medium to further easily infiltrate may be also used.

Also, in order to maintain survival of the cells, the medium should be added in a sufficient amount so that the 3D scaffold can be completely immersed therein, and the medium should be exchanged at a regular interval, even though this may vary with cell types, and the type of the medium should be also selected in views of the type which enables the cells to proliferate or differentiate optimally. In particular, a 3D culture method of culturing cells in an alginate bead may be applied as a part of measuring the signals of living cells using MRS according to an embodiment of the present invention.

Also, the cell may be seeded by adjusting the number of cells included in the 3D scaffold per unit capacity to a desired concentration, and as one example for overcoming low sensitivity of the MRS, a method of adjusting a concentration of cells to $2\times10^6$/ml or more to enable spectral signals of the cells to be observed in a magnetic field of 14.1 T may be included. In particular, it is preferable for the measurement method according to the present invention to apply an optimum concentration by differently adjusting the concentration of cells depending on machine because a size and resolution of signals vary with magnetic field strength of an MR machine which is used. A case in which an experiment is carried by applying the best concentration of cells ($1\times10^6$~$2\times10^6$/ml at 14.1 T) seeded according to the condition (magnetic field strength) of the MR machine used upon measurement to the 3D culture scaffold in the experiment of this present invention will be explained as an example.

Particularly, in order to noninvasively acquire the cell signals, a method of measuring the MRS of the 3D scaffold, the medium and the cells proliferated or differentiated during a constant period may be used without a process for separating the cells from the 3D scaffold.

In a container shown in FIGS. 2 and 3, the 3D scaffold, medium, and cells are cultured together, and MR measurement is performed with the container itself including the cultured contents. In the case of an immunochemical measurement method which is typically used, a process for separating the 3D scaffold and the cells from each other must be performed, whereas the MR measurement method according to the embodiment of the present invention may be performed at a time without the separating process. Thus, the cells may be prevented from being damaged and may be also reused.

The medium (30) is recommended and selected depending on cell types used and differentiation types, and should be generally exchanged every 3 or 4 days.

In a case in which alginate bead among the constituent materials of the aforesaid scaffold is used for the medium (30) of FIG. 2 is provided as an example, the alginate bead is fixed in a shape so as to support cells by performing a process of mixing a mixture of a medium and the cells to alginate solution in a ratio of 1 to 1 and a process of solidifying the mixed solution in calcium chloride, and thereafter a washing process is performed in order to remove the calcium chloride, and the medium is added in a sufficient amount so that the scaffold can be completely immersed therein, thereby culturing the cells.

In particular, in this case, when the cells and medium are mixed in the alginate solution, the number of cells included per unit capacity is adjusted so that a concentration suitable for experiments can be freely adjusted, thereby seeding the cells.

The alginate bead is solidified in a state in which the alginate, medium and cells are uniformly distributed, and as a result, the same amount of cells is seeded in each bead.

Based on this, the number of cells seeded in one bead may be checked, and as shown in FIG. 2, when the number of beads used upon MRS measurement is known, a total number of cells used in the experiment may be calculated. Thus, if the total number of cells may be figured out, the expression levels of metabolites can be compared by normalizing individually obtained spectra in a level of the same cell concentration, even though cell concentrations used upon MRS measurement are different from each other.

An MR spectrum apparatus for performing the cell differentiation measurement method in FIG. 2 may be formed in a structure illustrated in FIG. 3. The configuration of the apparatus is only one example, and the MRS to which the biomarker according to the present invention is applied is not limited thereto.

In order to perform the cell differentiation measurement according to the embodiment of the present invention, the amount of alginate beads to be measured using MRS may be formed to be fit into a RF coil (50) depending on an apparatus as shown in FIG. 3. For example, the alginate beads are placed in a measuring vessel (60) to be fit into a size of the RF coil (50) so that optimum signals can be acquired, and are distributed on the entire coil evenly.

The RF coil (50) for measuring MR signals may have various forms, for example, a solenoid form, a surface form, a quadrature form and the like.

The vessel (60) in FIG. 3 is used to hold the alginate and medium, and various vessels may be used depending on shapes and sizes of the coil. Also, the alginate bead in which cells are seeded, namely, the culture scaffold (20) may be measured in a state of being put in the vessel (60) to be distributed in the entire coil so that MR signals can be optimally acquired.

The cell differentiation measurement according to the embodiment of the present invention may be applied to a series of MR machine capable of noninvasively and nondestructively acquiring spectrum data, such as MRS and MRI. In addition, the MR signals may be measured by using a vessel in other forms, not a test tube for the MRS so as to be used in the MRI machine.

The measurement method using the MRS according to the present invention is a noninvasive method, and accordingly, it is advantageous in that the samples for which measurement is completed can be cultured again with the vessel, and thereafter, the same samples can be re-measured.

Moreover, according to the present invention, in order to distinguish the differentiation and proliferation of cells with the measurement method using the MRS, a method of ascertaining the type and size of metabolite peaks shown in spectra which are measurement results is used.

In particular, a reference metabolite which is changed depending on differentiation may be used as a biomarker for observing the differentiation of cells.

Specifically, the same substances are always shown at the same position (ppm) on an MR spectrum, and based on the fact that an amount of the substances is reflected in a size of the peak, a metabolite showing a change during the cell proliferation and differentiation is determined as a proliferation/differentiation marker (biomarker), and metabolites not showing a change are determined as signals of the 3D scaffold and medium.

In this case, integral values of the peaks shown in MR spectra may be calculated and compared, which is to monitor the change in metabolites during the cell proliferation and differentiation. Also, a method of normalizing data may be applied to quantitative analysis of the MRS as follows.

First, data has been obtained by including a reference material shown at 0 ppm with the same amount, and then a method of normalizing spectra by adjusting the reference material peaks in each of the spectra to the same size may be used.

However, in the present invention, in order to exclude a case in which a reference material is not included in the same amount, or a reference material capable of having a negative effect on the cells is used, it is preferable to use a method of normalizing the spectra to the number of cells measured from the same samples so as to be comparable in the same cell concentration by confirming the number of cells measured so that signals among the spectra are comparable in the same level as the method described above.

Since in such a method of normalizing the spectra to the number of cells, the number of cells is estimated regarding the measured respective samples, it is advantageous in that normalization for quantitative analysis can be performed even though the cells are not seeded in an amount which is determined at first due to a loss generated at the time of seeding the cells.

In addition, with regard to a method of estimating the number of cells in order to compare and ascertain a relationship between quantitative analysis of the MRS and cell proliferation/differentiation, a general method such as cell counting with a hematocytometer and DNA assay may be used. As the cell concentration seeded in each alginate bead is identical to each other, a total number of cells used in the experiment may be calculated even if cell counting is performed with only one alginate bead.

According to the present invention, the proliferation/differentiation states of the cell samples may be evaluated based on a change in metabolites determined by obtaining and comparing MRS data depending on the cell proliferation/differentiation periods. The metabolites used therein may become a biomarker which may show the cell proliferation/differentiation states. The biomarker using such a metabolite may be applied to various cells when the concentration of cells measured is known, and thus the proliferation/differentiation states may be evaluated by comparing integral values of the metabolite and the biomarker.

Furthermore, as the metabolite varies with cell types, the cell types may be identified, and whether or not differentiation is progressed into targeted cells. Cell differentiation process may be also evaluated.

Hereinafter, the point of the present invention will be described in detail based on various measurement data results for cells.

Figure 4:
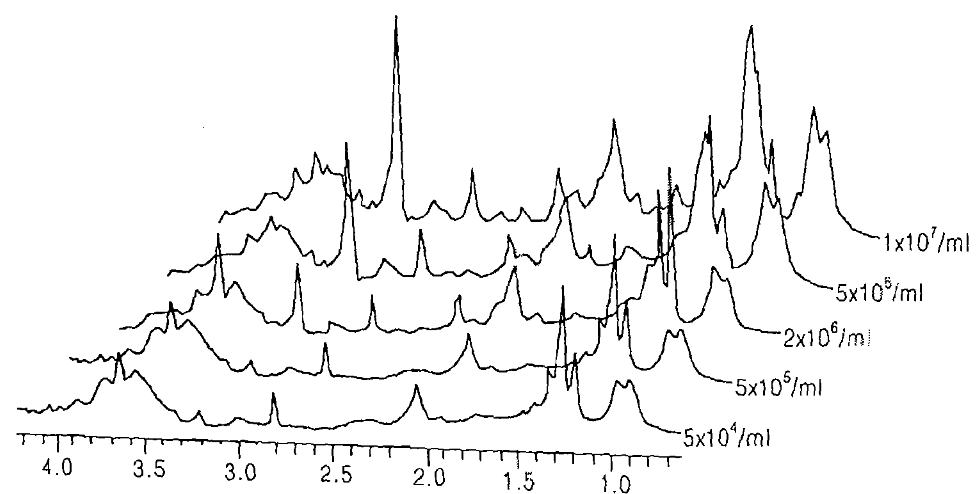
FIG. 4 illustrates changes in MRS signals depending on each cell concentration tested for acquiring signals of human mesenchymal stem cells (hereinafter referred to as 'hMSCs') using MRS according to an embodiment of the present invention.

FIG. 4 illustrates spectroscopy data (spectrum) obtained after seeding hMSCs having different concentrations in order to test low MR sensitivity for 3D cultured cells, and according to the data of FIG. 4, an optimum cell concentration, which enables MR signals of the cells to be acquired, may be determined.

Making the cell concentrations differently seeded may be completed by differing in number of the cells included per unit capacity as indicated above, and the concentrations may range from $1\times10^6$ to $1\times10^7$/ml or may be broad beyond the range. Also, a cell proliferation measurement standard may be determined by measuring and analyzing a change in metabolites depending on the number of cells after seeding the cells in the same amount in 3D scaffolds by differing in concentrations of the cells.

According to FIG. 4, when an MR machine of 14.1 T was used, only peaks derived from a cell medium and alginate were observed at a concentration of $5\times10^5$/ml or less, but peaks of the cells were not detected. However, at the concentration of $2\times10^6$/ml or more, intensities of the cell peaks were observed to increase as the peaks could be observed with naked eyes at 3.22 ppm and 2.35 ppm, and the intensities of the cell peaks were continuously increased. Thus, by calculating integral values for each peak and comparing change amounts, this may be used as a marker capable of evaluating cell proliferation and differentiation. In particular, in the case of phosphocholine showing a peak of 3.22 ppm, this is a metabolite peak which does not overlap with medium and alginate peaks, and accordingly, the phosphocholine may be utilized as a proliferation and differentiation marker.

FIGS. 5 to 9 are spectroscopy data (spectrum) resulting from measuring cell signals in a chondrogenesis period by applying the aforesaid 3D culture method according to the present invention.

Figure 5:
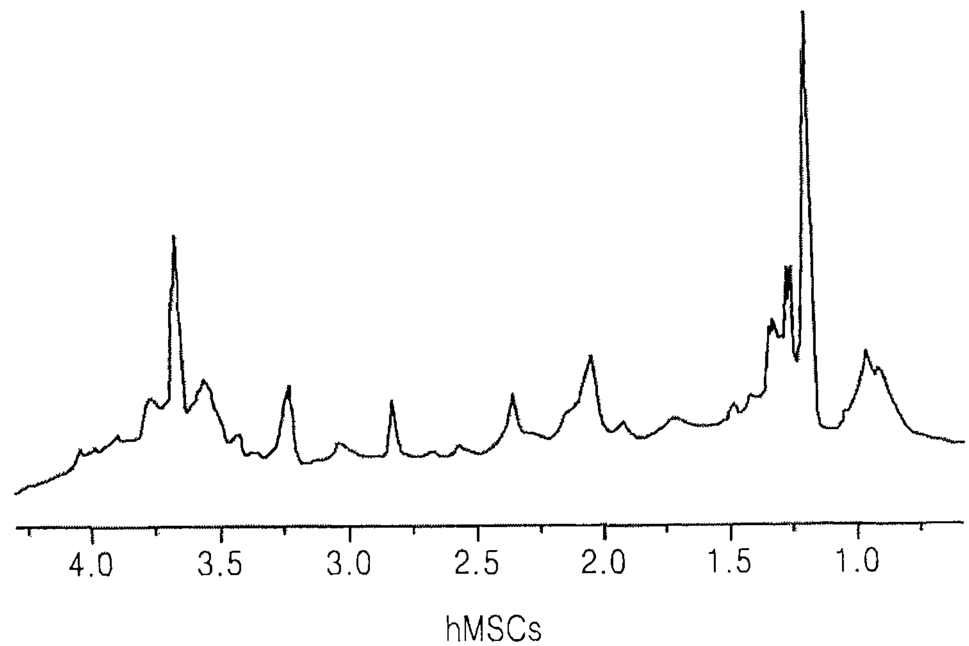
FIG. 5 illustrates MRS data (spectrum) obtained from undifferentiated hMSCs according to an embodiment of the present invention.
Figure 6:
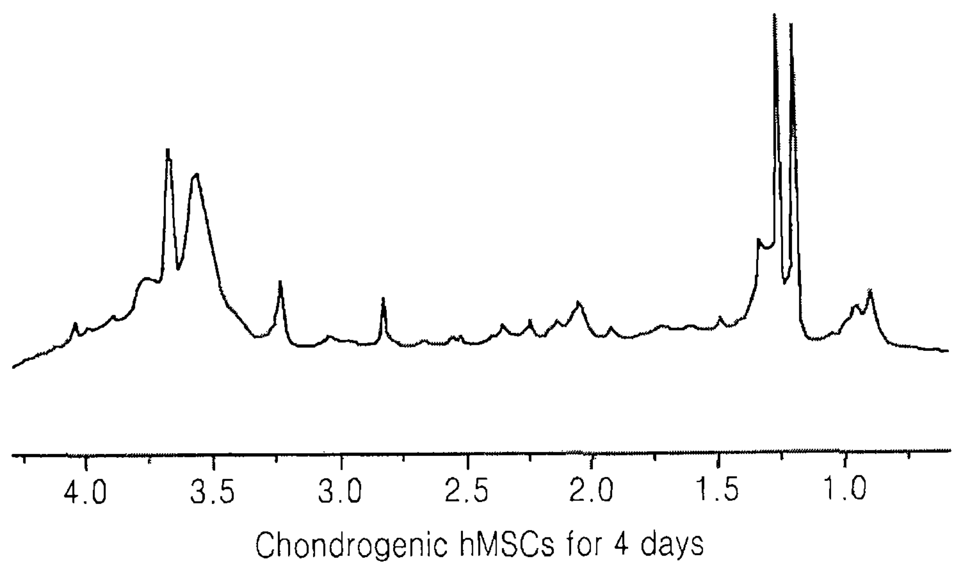
FIG. 6 illustrates MRS data (spectrum) obtained by inducing differentiation from hMSCs into chondrocytes for 4 days according to an embodiment of the present invention.
Figure 7:
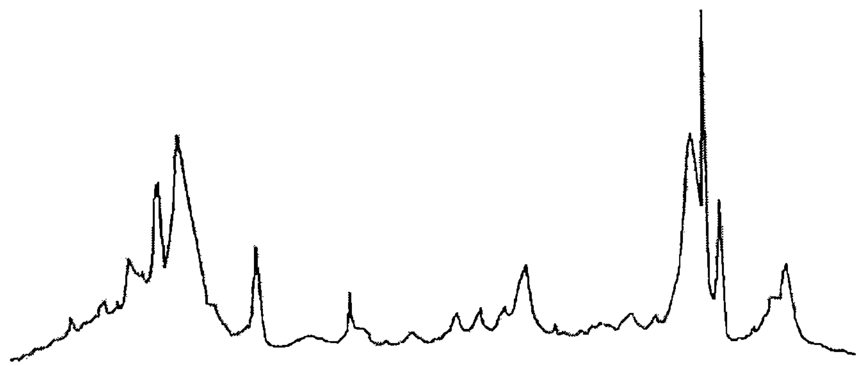
FIG. 7 illustrates MRS data (spectrum) obtained by inducing differentiation from hMSCs into chondrocytes for 7 days according to an embodiment of the present invention.
Figure 7:
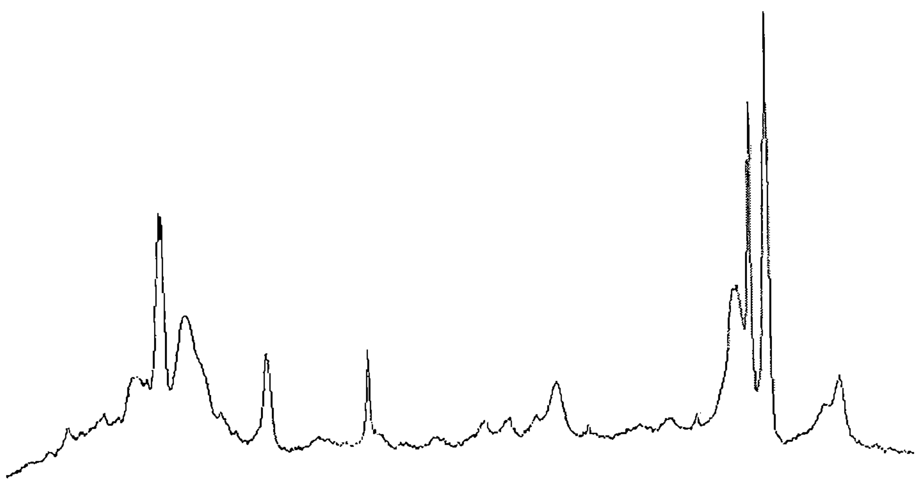
Figure 8:
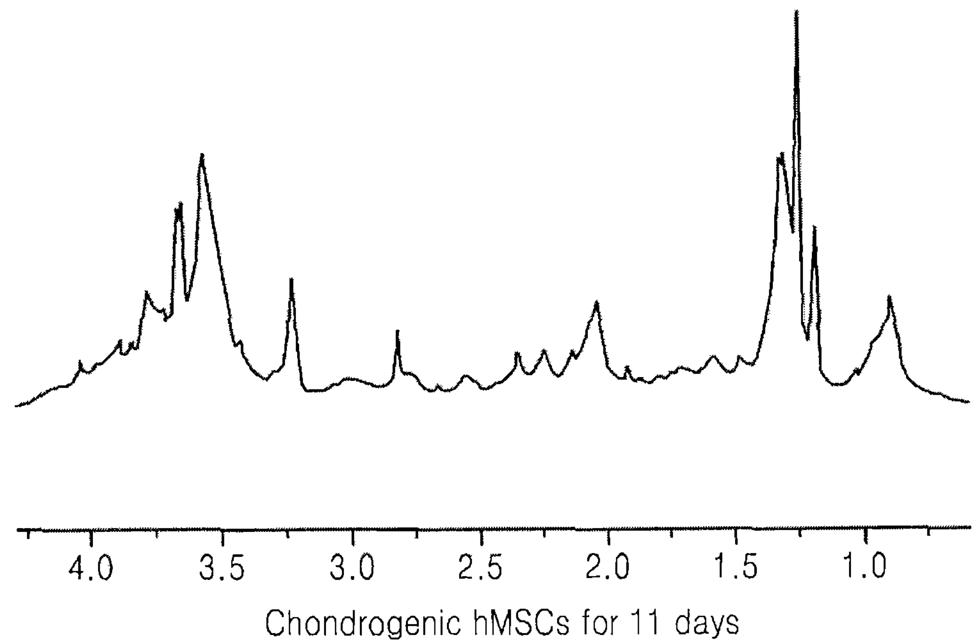
FIG. 8 illustrates MRS data (spectrum) obtained by inducing differentiation from hMSCs into chondrocytes for 11 days according to an embodiment of the present invention.
Figure 9:
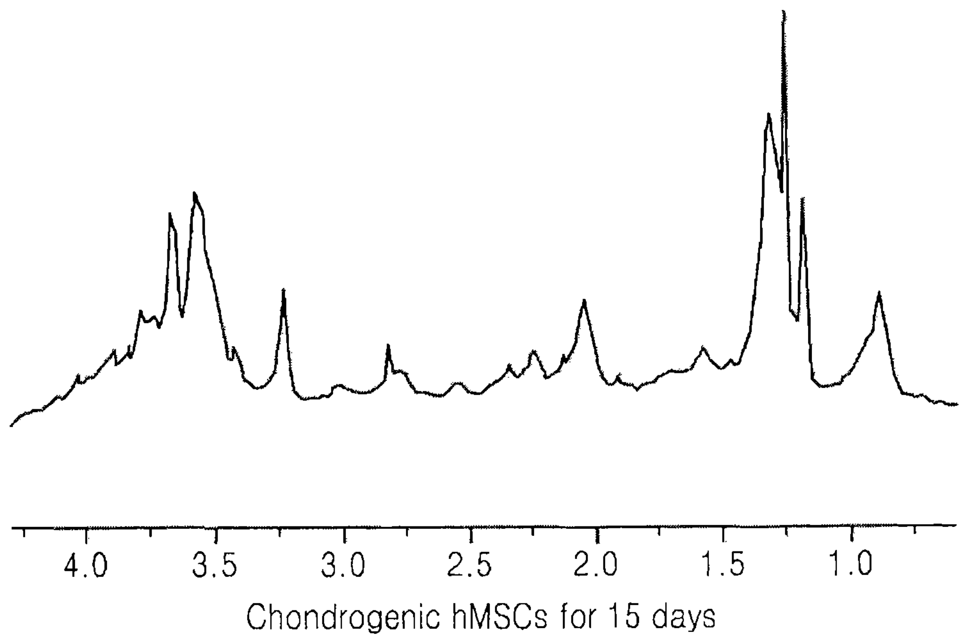
FIG. 9 illustrates MRS data (spectrum) obtained by inducing differentiation from hMSCs into chondrocytes for 15 days according to an embodiment of the present invention.

FIG. 5 illustrates a first spectrum resulting from applying a cell culture method to hMSCs, FIG. 6 illustrates a spectrum of chondrogenic hMSCs for 4 days, FIG. 7 illustrates a spectrum of chondrogenic hMSCs for 7 days, FIG. 8 illustrates a spectrum of chondrogenic hMSCs for 11 days, and FIG. 9 illustrates a spectrum of chondrogenic hMSCs for 15 days. The biomarker for cell differentiation measurement using the MRS may be determined by performing quantitative analysis of the respective metabolites based on the spectroscopy data (spectra) resulting from measuring cell signals in the chondrocyte differentiation periods.

That is, based on the spectral peaks are always shown at the same positions (ppm) in the MRS regarding the same types of metabolites, and the amount of metabolites is reflected in the integral values of the spectral peaks, the biomarker for the MRS according to the present invention may have unique values depending on cell types and differentiation degree.

The spectroscopy data (spectrum) obtained for quantitative analysis depending on the type of metabolites should proceed with a normalization process as previously described. With regard to such a normalization process, a method of adding a reference material shown at a peak of 0 ppm in the same amount and normalization of remaining peaks on the basis of the added reference material may be applied.

Meanwhile, with respect to the normalization method according to a preferred embodiment of the present invention, a method of estimating the number of cells without the addition of a reference material and normalizing spectra to the number of cells may be used. When the normalization method is used, the spectra may be normalized even if the reference material is added in different amounts, and cell loss may be prevented because the reference material capable of damaging cells is not included. The normalization method based on the number of cells is advantageous in that proliferation/differentiation states may be decided when the types of undifferentiated cells used are the same and the types of differentiated cells are the same, even though the cells are seeded in different concentrations (different experimental conditions).

Figure 10:
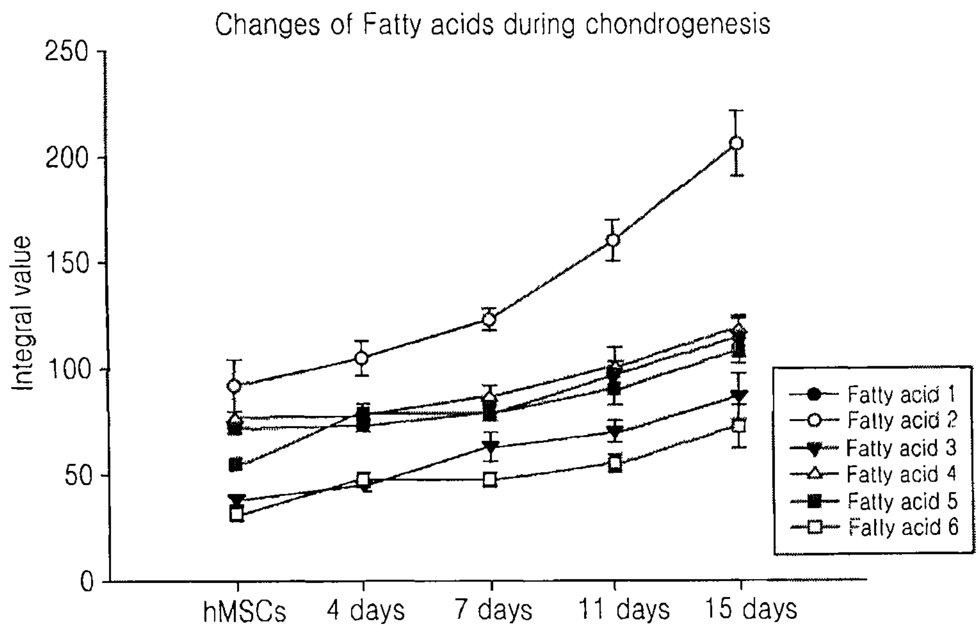
FIG. 10 is a graph in which changes in spectrum peaks of fatty acids 1 to 6 shown in MRS data of hMSCs were measured according to an embodiment of the present invention.
Figure 11:
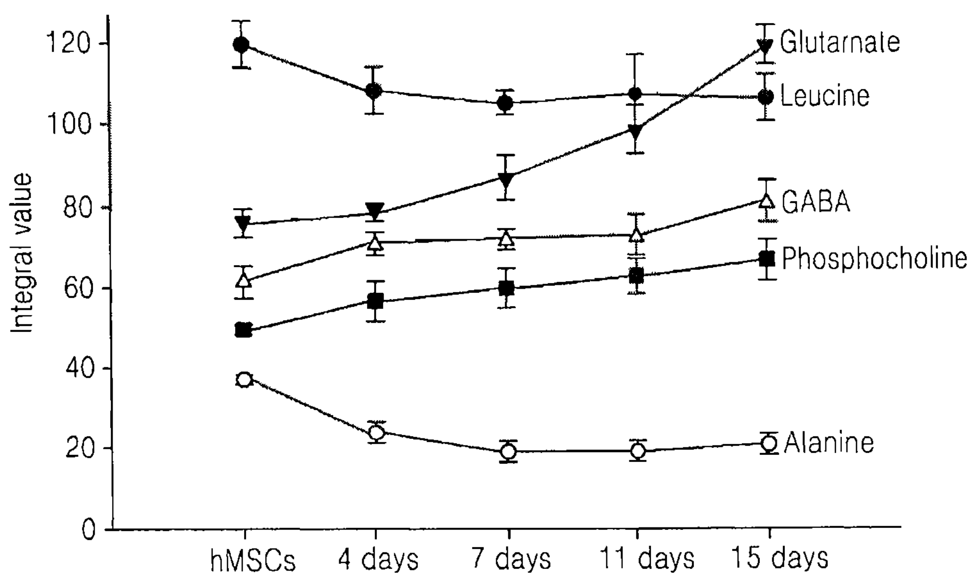
FIG. 11 is a graph in which changes in metabolites except the fatty acids shown in MRS data of chondrogenic hMSCs were measured according to an embodiment of the present invention.

Applied the aforesaid method according to the present invention, a differentiation marker capable of noninvasively monitoring a cell differentiation may be determined by the quantitative comparison of changes in metabolites on the spectra shown in FIGS. 5 to 9 by the method of normalizing the spectra to the concentration of cells. Meanwhile, there is a need to remove a $H_2O$ signal which is relatively largely observed compared to other signals for analyzing cell signals, and this may settled by using an MR pulse sequence having a function to suppress the $H_2O$ signal. FIGS. 10 and 11 are graphs showing the change amounts (integral values of peaks) of metabolites having a change in the spectroscopy data (spectrum) obtained in the chondrogenesis period shown in FIGS. 5 to 9, and a differentiation degree may be observed by monitoring a change aspect of the respective metabolites. According to FIG. 10, a change amount of each of the fatty acids was gradationally observed by each differentiation period, and a fatty acid (fatty acid 2) of 1.30 ppm showed the biggest change compared to other metabolites. Based on this, a chondrogenesis degree may be evaluated by monitoring the fatty acid of 1.30 ppm depending on differentiation periods through MRS measurement of the samples seeded in the same concentration.

Also, according to FIG. 11, metabolites (alanine and leucine) whose amount is reduced after chondrogenesis, and thereafter is uniformly maintained, may be found. These metabolites may be used as a differentiation marker for determining chondrogenesis. Meanwhile, since phosphocholine shown in FIG. 11 was also observed to gradationally increase in amount during the chondrogenesis period, the phosphocholine may be also used as a differentiation marker capable of showing chondrogenesis states depending on each differentiation induction period. Accordingly, peak values of the metabolites such as leucine, alanine, phosphocholine, glutamine, and GABA may be used as a biomarker for chondrogenesis.

Figure 12:
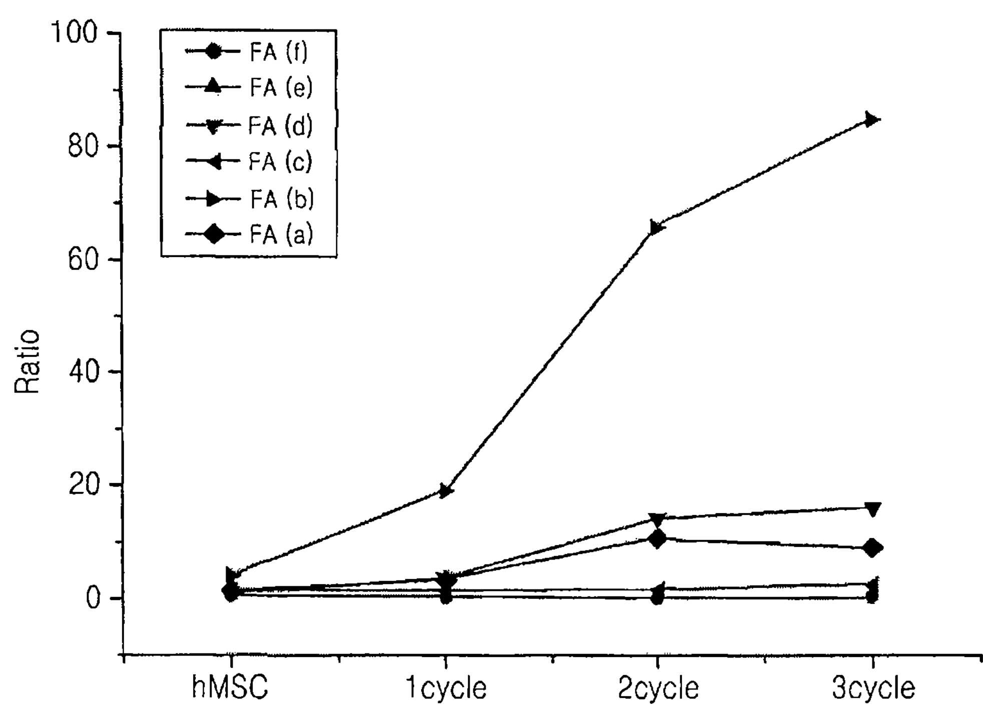
FIG. 12 is a graph in which changes in fatty acids shown in MRS data of adipogenic hMSCs were measured according to an embodiment of the present invention.

FIG. 12, as another embodiment of the present invention, is a graph illustrating a change amount in peak integral values of the fatty acid metabolite spectra showing a variation in spectra changed in a period when hMSCs are differentiated into adipocytes, and a differentiation degree may be observed by monitoring an aspect of the change for each metabolite.

According to FIG. 12, it can be observed that most of fatty acids increased, and in particular, the fatty acid (b) showed the largest change, which the fatty acid is the fatty acid of 1.30 ppm that is the same ingredient as fatty acid 2 shown in FIG. 10. The fatty acid 2 in FIG. 10 showed a change of about 2 times, whereas the fatty acid (b) of FIG. 12 showed an increase of about 16 times during the same differentiation period as shown in FIG. 10, and thus, the fatty acid could be ascertained to largely increase in adipogenesis compared to chondrogenesis. Accordingly, the chondrogenesis and the adipogenesis may be distinguished from each other by metabolite measurement according to the embodiment of the present invention, and the fatty acid 2 may be utilized as a useful marker for discriminating the types of differentiations. In comparing the aforesaid FIG. 5 and FIG. 12, the method of normalizing the spectra may be applied based on the concentrations of the cells rather than the reference material for the MRS. That is, since the quantitative analysis is performed after the normalization process to the number of cells, when the differentiation periods are identical to each other, quantitative comparison may be practicable even if the numbers of cells and the increase amounts of cells are different.

The cell differentiation marker for the MRS determined according to the embodiment of the present invention may be applied to other differentiations as well as the chondrogenesis and adipogenesis carried out in the present invention.

Other metabolites found in different differentiation processes may be utilized as differentiation markers.

Also, a metabolite used as a biomarker for MR may be changed depending on cell types used and differentiation types. That is, with regard to the cell differentiation marker for the MRS, various metabolites are found depending on cell types and differentiation types, and thus, all metabolites showing a change associated with proliferation/differentiation in the MRS data measured during cell culture may be applied as the cell differentiation marker for the MRS according to the present invention.

In other words, the examples described above as the embodiments and experimental examples of the present invention show that one of the metabolites obtained from the cell samples for inducing a differentiation from hMSCs into chondrocytes may be applied as a biomarker. For example, any one metabolite selected from among fatty acids, leucine, alanine, phosphocholine, glutamine, and GABA may be used as a biomarker, and a fatty acid of 1.30 ppm may be used as a biomarker for chondrogenesis and adipogenesis. However, the metabolites are not limited thereto. Since there are various metabolites which can be found depending on cell types and differentiation types, a variety of metabolites may be applied as a biomarker, and a combination of change aspects of various metabolites rather than one metabolite may be also applied as a biomarker.

Accordingly, the point of the present invention may include all constitutive elements for determining cell proliferation and differentiation degrees by measuring MRS signals from cells using MRS, normalizing the MRS signals to the concentration of measured cells, and comparing metabolites showing changes on the spectra measured during the cell differentiation process.

Also, according to the present invention, experiments can be repeatedly performed using the same samples without the loss of cells, and cell states can be evaluated using MRS data obtained without a separate staining and chemical reaction process so that reproducibility of experiments can be improved, an experiment process can be simplified and the experimental cost can be reduced.

As previously described, in the detailed description of the invention, having described the detailed exemplary embodiments of the invention, it should be apparent that modifications and changes can be made by persons skilled without deviating from the spirit or scope of the invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims and their equivalents.

What is claimed is:

1. A noninvasive measurement method of cell proliferation and differentiation states using nuclear magnetic resonance spectroscopy (NMR), comprising:

preparing a cell sample by three-dimensionally culturing the cell in a scaffold immersed in a liquid medium; repetitively measuring NMR signals from the same cell sample over time using an NMR depending on a specific cycle during a culturing period; normalizing the NMR signals to a concentration of the measured cells; and determining a biomarker for evaluating cell proliferation and differentiation degrees through comparison of metabolites showing changes on spectra measured during a proliferation and differentiation process of the cells.

2. The noninvasive measurement method of claim 1, wherein the normalization comprises normalizing the spectra of metabolites obtained during the proliferation and differentiation process of the cells to the number of cells, and wherein determining the biomarker for evaluating cell proliferation and differentiation degrees comprises comparing integral values of peaks of the normalized metabolites.

3. The noninvasive measurement method of claim 1, wherein the biomarker is one metabolite or two or more metabolites obtained from cell samples to which a differentiation from human mesenchymal stem cells (hMSCs) into chondrocytes is induced, or a combination of change aspects of the metabolites is used as the biomarker.

4. The noninvasive measurement method of claim 3, wherein the biomarker is one metabolite selected from among fatty acids, leucine, alanine, phosphocholine, glutamine, and GABA, or a combination of change aspects of the metabolites is used as the biomarker.

5. The noninvasive measurement method of claim 3, wherein determining the biomarker includes using a fatty acid of 1.30 ppm as a biomarker for chondrogenesis.

6. The noninvasive measurement method of claim 3, wherein determining the biomarker includes using a fatty acid of 1.30 ppm as a biomarker for adipogenesis.

7. A cell proliferation and differentiation marker for NMR used in a measurement method of claim 1, which evaluates cell proliferation and differentiation information by analyzing NMR data obtained from cell samples.

8. The cell proliferation and differentiation marker of claim 7, wherein one of various metabolites showing changes associated with proliferation and differentiation in NMR data measured during cell culture or a combination thereof serves as a standard for evaluating proliferation and differentiation degrees.

9. The noninvasive measurement method of claim 1, wherein the repetitively measuring of NMR signals from the same cell sample occurs without separating the cells from the scaffold.

* * * * *